(12) United States Patent
Read et al.

(10) Patent No.: US 6,183,784 B1
(45) Date of Patent: Feb. 6, 2001

(54) METHOD OF AMELIORATING ALIMENTARY TRACT DAMAGE DUE TO CHEMOTHERAPY OR RADIATION

(75) Inventors: Leanna Christine Read, Kensington Park; Gordon Stanley Howarth, Hillbank, both of (AU)

(73) Assignee: GroPep Limited, Thebarton (AU)

( * ) Notice: Under 35 U.S.C. 154(b), the term of this patent shall be extended for 0 days.

(21) Appl. No.: 08/894,200

(22) PCT Filed: May 2, 1996

(86) PCT No.: PCT/AU96/00253

§ 371 Date: Aug. 14, 1997

§ 102(e) Date: Aug. 14, 1997

(87) PCT Pub. No.: WO96/34614

PCT Pub. Date: Nov. 7, 1996

(30) Foreign Application Priority Data

May 2, 1995 (AU) .................................................. PN 2712

(51) Int. Cl.⁷ .................................................... A61K 35/20
(52) U.S. Cl. .................. 424/535; 514/2; 514/21
(58) Field of Search ........................... 514/2, 21; 424/535

(56) References Cited

FOREIGN PATENT DOCUMENTS

| | | |
|---|---|---|
| 1735388 | 12/1988 | (AU) . |
| 651283 * | 7/1994 | (AU) . |
| 375852 * | 7/1990 | (EP) . |
| 502213 * | 9/1992 | (EP) . |
| 527283 | 2/1993 | (EP) . |
| 9001941 | 3/1990 | (WO) . |
| 9200994 | 1/1992 | (WO) . |
| 9208480 | 5/1992 | (WO) . |
| 9218153 | 10/1992 | (WO) . |
| 9325227 | 12/1993 | (WO) . |
| 9423032 | 10/1994 | (WO) . |
| 9500155 | 1/1995 | (WO) . |
| 9529933 | 11/1995 | (WO) . |

OTHER PUBLICATIONS

Kinnen, et al., "Gastroprotection with Milk Phospholipids: A First Human Study" Milchwissenschaft, vol. 47, No. 11 (1992) pp. 694–696.

M.W.L. Koo, "The Effects of Milk and Calcium on Ethanol–Induced Gastric Mucosal Damage" Pharmacological Research, vol. 29, No. 3 (Mar. 29, 1994) pp. 217–224.

* cited by examiner

Primary Examiner—Jean C. Witz
(74) Attorney, Agent, or Firm—Ladas & Parry (57) ABSTRACT

A milk product extract composiiton including a plurality of cell growth stimulating factors, extracted from milk product, in concentrated form; said factors having basic to approximately neutral isoelectric points. Cell culture compositions and pharmaceutical or veterinary compositions including the above milk product extract. Methods for preparing and using the same.

20 Claims, 4 Drawing Sheets

Fig 1a

*: $P<0.05$ vs Methotrexate-treated Controls (0 mg/day GFE-2)

Fig 1b

*: $P<0.05$ vs Methotrexate-treated Controls (0 mg/day GFE-2)

METHOD OF AMELIORATING ALIMENTARY TRACT DAMAGE DUE TO CHEMOTHERAPY OR RADIATION

This invention relates to the prophylaxis, amelioration and/or treatment of damage to the lining of the alimentary tract resulting from chemotherapy and/or radiation.

Chemotherapy and/or radiotherapy are effective at destroying tumours because they target fast-growing tissues. The mechanism involves impairment of DNA synthesis or interference with metabolic processes required for rapidly dividing cells. While tumour cells are selectively targeted by anticancer treatments, the fast-growing tissues of the host are also susceptible, particularly the immune cells of the body and the lining of the alimentary tract. Epithelial cell division in the alimentary tract occurs in the crypt zone of the mucosa. The newly synthesised cells then acquire their functional properties (such as digestive enzymes) as they migrate towards the luminal surface and finally, they are extruded into the lumen of the alimentary tract. This entire process takes only several days so that the mucosal epithelium of the alimentary tract has one of the most rapid rates of cell division of any body tissue, and is therefore a major site of toxicity for anticancer regimens.

The linings of the mouth and oesophagus are particularly sensitive to chemotherapy and radiation. The oral ulcerations characteristic of mucositis (also referred to as 'stomatitis') are a major clinical problem causing considerable pain, increased susceptibility to infection and inability to eat. Damage to the intestinal lining also occurs commonly in the small bowel, and less frequently in the large bowel, leading to severe diarrhoea and pain. (Verdi C J 1993 Cancer therapy and oral mucositis. An appraisal of drug prophylaxis. Drug Safety 9:185–195; Sonis S T 1993 Oral complications of cancer chemotherapy In VT DeVita Jr, S Hellman and S A Rosenberg (ed) Cancer, Principles and Practice of Oncology, pp 2385–2394. Philadelphia, J B Lippencott Co).

Mucositis occurs by two distinct mechanisms: by direct damage to the alimentary lining by anticancer drugs or radiation, and indirectly as a result of opportunistic infections associated with neutropenia in patients with a compromised immune system. As a result, any drug that causes significant neutropenia can precipitate indirect mucositis (Verdi C J 1993). Direct damage to the gut barrier would also increase susceptibility to opportunistic infections by allowing bacterial translocation across a damaged gut lining.

In general, mucositis is manifest within 5 to 10 days of the drug or radiation treatment and can last several weeks. The severity of mucositis can vary from mild to so severe that it limits the dose of chemotherapy or radiation. For patients undergoing high-dose chemo/radiation therapy, mucositis is the chief source of infection and the resultant sepsis, the main cause of morbidity and mortality, and the primary reason for their hospitalisation. Patients suffering mucositis may need several weeks or more of intravenous feeding as a result of the mouth ulcers, cramps, extreme pain, gut denuding, and severe diarrhoea (Verdi 1993; Sonis 1993).

Mucositis can delay retreatment of patients with chemotherapy or radiotherapy or necessitate a subsequent dose reduction, thereby compromising the overall efficacy of anticancer treatment. With some anticancer regimens, mucositis is the limiting toxicity. Overcoming this toxicity would improve quality of life, reduce susceptibility to secondary infection, obviate the need for intravenous feeding, and importantly, improve the efficacy of tumour ablation through increased tolerance to higher doses of chemotherapy or radiation (Verdi C J 1993). Costs of hospitalisation would be substantially reduced as more patients could be managed as out-patients.

About 40% of all patients receiving chemotherapy develop significant mucositis, with up to 100% incidence in some forms of chemotherapy or radiotherapy. Clinically significant mucositis develops with a range of standard chemotherapy drugs that are used, either alone or in combination, to treat various cancers including those of the colon, breast, prostate, head, neck and haemopoetic system. Examples of drugs that frequently cause direct mucositis include, but are not limited to, alkylating agents such as mechlorethamine, melphalan and busulphan, antimetabolites including cytarabine, floxuridine, 5-fluorouracil, mercaptopurine, methotrexate and thioguanine, cytotoxic drugs such as bleomycin, actinomycin-D, daunorubicin, etoposide, mitomycin, vinblastine and vincristine, and other chemotherapy drugs such as hyroxyurea and procarbazine (Sonis 1993). Direct exposure of the alimentary tract to high-dose radiotherapy, as occurs for example with total body irradiation, treatment of head and neck tumours or radiotherapy of abdominal tumours, will also cause a high incidence of mucositis.

Mucositis is particularly severe with high-dose chemotherapy or when two or more drugs are used in the one course of treatment, for example the ablative therapy prior to bone marrow transplant or peripheral stem cell transplant. The combination of high-dose chemotherapy with aggressive radiotherapy can also cause severe mucositis (Sonis 1993).

The prior art suffers from the lack of an effective drug to prevent, reduce or treat damage to the lining of the alimentary tract resulting from chemotherapy and/or radiation. At present, patient treatment is mainly palliative to control pain through analgesics, prevent infection and provide intravenous nutritional support.

The prior art includes a number of approaches aimed at reducing the severity of mucositis. Low energy laser treatment of the mouth has been reported to reduce the severity of oral mucositis in patients given high dose chemotherapy prior to bone marrow transplantation (Ninth Annual Meeting of the International Soc. Oral Oncology, June 1994, NIH, Bethesda, USA). Numerous drugs have been evaluated in the prevention of mucositis, with some degree of efficacy for cytoprotectants (e.g. sucralfate) and antimicrobial drugs such as chlorhexidine and benzydamine (reviewed in Verdi C J 1993). A somatostatin analogue (octreotide acetate) has been shown to inhibit secretory diarrhoea in patients with mucositis induced by the chemotherapy drug, 5-fluorouracil. The mechanism of action is probably secondary to inhibition of pancreatic and gastrointestinal function (Petrelli N J, Rodriguez-Bigas M, Rustum Y, Herrara L, Creaven P 1993 Bowel rest, intravenous hydration and continuous high-dose infusion of octreotide acetate for the treatment of chemotherapy-induced diarrhoea in patients with colorectal carcinoma. Cancer. 72:1543–1546).

Recombinant transforming growth factor-beta 3 (TGF-b 3) has been shown to reduce the severity of oral mucositis induced by injection of hamsters with 5-fluorouracil (Sonis S T, Lindquist L, Van Vugt A, Stewart A A, Stam K, Qu G - Y, Iwata K K, Haley J D 1994 Prevention of chemotherapy-induced ulcerative mucositis by transforming growth factor-b3. Cancer Res. 54:1135–1138). The effects of other growth factors are less clear. For example, recombinant epidermal growth factor (EGF) does not appear to relieve oral mucositis (Sonis S T, Costa J W, Evitts S M, Linquist L E, Nicolson M 1992 Effect of epidermal growth factor on ulcerative mucositis in hamsters that receive cancer chemotherapy. Oral Surg Oral Med Oral Pathol. 74:749–755), but may enhance intestinal recovery following abdominal radiation (McKenna K J, Ligato S, Kauffman G L, Abt A B, Stryker J A, Conter R L 1994 Epidermal growth factor enhances intestinal mitotic activity and DNA content after acute abdominal radiation. Surgery. 15:626–632).

The prior art also includes International Patent Application PCT/SE93/00503) to Kabi Pharmacia. This application discloses the use of insulin-like growth factor-II (IGF-II) or effective analogues thereof for the manufacture of a medicament for prevention or treatment of nutritional or gastrointestinal diseases and for promoting human or animal neonatal growth. However, utility in the prophylaxis, amelioration and/or treatment of damage to the lining of the alimentary tract resulting form chemotherapy and/or radiation is neither disclosed or suggested.

The prior art also includes WO92/00994 A1 to GroPep Pty Ltd. This application discloses the use of a milk product extract for the treatment of gastrointestinal injury, disease or ulcers. However, utility in the prevention or treatment of damage to the alimentary tract resulting from chemotherapy or radiotherapy is neither disclosed nor suggested in this citation. Prior art in the field of mucositis, the most common injury from chemotherapy and/or radiotherapy predicts that it would be beneficial to reduce rather than increase the growth rate of the lining of the alimentary tract, and thereby render the cells less susceptible to chemotherapy or radiotherapy that targets rapidly growing tissues. This is the opposite effect to that which is predicted to occur with agents that heal or promote the regrowth of gastrointestinal tissues such as the plurality cell growth stimulating agents described in WO92/00994 A1. Accordingly the approach taken by the applicants in treating mucositis is contrary to the normal approach.

WO92/00994 A1 does not teach or disclose the use of a milk product extract for the amelioration or treatment of mucositis because the mechanism of alimentary tract damage in mucositis (inhibition of cell proliferation and neutropenia) is different from that which occurs in other alimentary tract conditions. For example, gastric ulcers, the treatment of which by milk products is described in the prior art, are not caused by an inhibition of cell proliferation nor are they accompanied by neutropenia Rather, they result from acid-induced destruction of the lining of the stomach. Mucositis of the mouth and esophagus is outside the region of the alimentary tract also claimed in WO92/00994A1, which only refers to the gastrointestinal tract (stomach and intestines). Since the structure of the epithelial lining of the mouth and esophagus is different from that in the stomach and intestines, an agent that reduces damage to the lining of the gastrointestinal tract cannot be predicted to have the same action in the mouth and esophagus.

It is an object of the present invention to overcome or at least alleviate one or more of the difficulties or deficiencies related to the prior art.

In a first aspect, the present invention provides a method for preventing, ameliorating and/or treating damage to the lining of the alimentary tract resulting from chemotherapy and/or radiation, which method includes administering to a patient in need thereof an effective amount of a milk product extract.

In the second aspect, the present invention provides a pharmaceutical or veterinary composition for preventing, ameliorating and/or treating damage to the lining of the alimentary tract resulting from chemotherapy and/or radiation, said composition including an effective amount of a milk product extract and a pharmaceutically or veterinary acceptable diluent, carrier or excipient, therefor.

The present invention may be useful for research purposes including administration of milk product extract to animals with experimental damage to the lining of the alimentary tract. For example, the invention may be used in hamsters with 5-fluorouracil-induced oral or large bowel mucositis, or rodents with intestinal mucositis induced by radiation or chemotherapy drugs such as cytarabine or etoposide. The present invention may also be useful, for example, in cell culture to protect or treat epithelial cells cultured from the oral, oesophageal or gastrointestinal lining from chemotherapy or radiation-induced damage.

Accordingly in a third aspect, the present invention provides a method for preventing, ameliorating and/or treating damage to epithelial cells cultured from the lining of the alimentary tract resulting from treatment of said cells with a chemotherapeutic agent and/or radiation, which method includes culturing said cells in the presence of a milk product extract.

By "damage" is meant any alteration in normal structure or function. Such damage includes mucositis, at least partial loss of mucosal crypt area and/or mucosal villus length, or an increase in bacterial translocation across the alimentary tract.

The term "alimentary tract" as used herein refers to the digestive passage in any animal from mouth to anus and includes mouth, oesophagus and gastrointestines (including stomach, small and large bowel). In a preferred aspect, the present invention is particularly applicable to the mouth and/or oesophagus.

By "lining" is meant any biological material which covers a surface or lines a cavity or the like and which performs protective, screening and/or other functions. The lining of the alimentary tract includes the oral, oesophageal and gastrointestinal epithelia.

By "an effective amount" is meant a quantity of milk product extract which will upon single or multiple dose administration to the patient be effective in the prophylaxis, amelioration and/or treatment of damage to the lining of the alimentary tract resulting from chemotherapy and/or radiation.

By "preventing, ameliorating and/or treating" is meant
(a) in the case where the milk product extract is administered before the damage occurs, a reduction or elimination of subsequent damage compared with the damage which would have occurred if the milk product extract was not administered; and
(b) in the case where the milk product extract is administered after the damage has occurred, a reduction or elimination of such damage.

By a "pharmaceutically or veterinarily acceptable diluent, carrier or excipient" is meant a diluent carrier or excipient which is compatible with the other ingredients of the composition and not injurious to the patient.

The term "milk product" as used herein refers to a derivative from human or animal milk in which the proportions of fat and/or protein constituents thereof are altered. Examples of milk products include milk whey, skim milk, colostral whey, cheese whey and acid (casein) whey. In a preferred aspect, the milk product may be from an ungulate mammal.

The term "milk product extract" as used herein refers to an extract from human or animal milk product in which the proportions of salt, fat and/or main protein constituents thereof are altered. The milk product extract may be a cheese whey extract, a colostral whey extract, a skim milk extract or an acid (casein) whey extract. Examples of milk product extracts include ultrafiltrates of milk products or milk products that have been subjected to adsorption and to elution from chromatography matrices. Preferably the milk product extract is prepared by subjecting a milk product to cation exchange chromatography, for example by the method described in Australian Patent 645,589.

Preferably the milk product extract is a milk product extract composition including a plurality of cell growth stimulating factors, extracted from milk product, in concentrated form; said factors having basic to approximately neutral isoelectric points. More preferably the milk product extract is a milk product extract composition including a mixture of cell growth factors having basic to about neutral isoelectric points (eg. isoelectric points between approximately 6.0 and approximately 10.5), wherein the mixture of cell growth factors is obtained from a milk product of an ungulate mammal, and wherein the milk product is subjected to a cation exchange matrix under conditions whereby casein, α lactalbumin, and β lactoglobulin present in the milk product are not adsorbed to the matrix, after which the adsorbed growth factor mixture is eluted with a substantially aqueous salt solution and then optionally concentrated.

Preferably the milk product extract composition is a cheese whey extract composition.

The cheese whey extract composition may be formed from cheese whey wherein the proportions of the main protein constituents thereof are altered.

The milk product extract may include less than approximately 1% w/w casein, α lactalbumin or β lactoglobulin, based on the total weight of the extract.

More preferably the milk product extract is a cheese whey extract prepared by the method described in Australian Patent 645589, the entire disclosure of which is incorporated herein by reference. This includes GFE and GFE-2 as described in Australian Patent 645589.

The milk product extract may include lactoperoxidase and/or lactoferrin. Preferably the milk product extract including lactoperoxidase and/or lactoferrin is prepared by adsorption of a milk product to and elution from one or more chromatography matrices, for example a cation exchange matrix. Those familiar with the art will recognise that lactoperoxidase and lactoferrin are major protein components in GFE and lactoperoxidase is a major protein component in GFE-2 as described in Australian Patent 645,589.

The milk product extract may be modified to enhance activity, including but not limited to transient acidification and/or purification under acidic conditions, for example using molecular sieve chromatography or controlled pore ultrafiltration, as described in International Patent Application No. PCT/AU95/00237, the entire disclosure of which is incorporated herein by reference.

Accordingly, in an alternative preferred form the milk product extract is a milk product extract composition including a plurality of modified milk growth factors having isoelectric points above approximately 6.0 and molecular weights in the range of approximately 5000 to 30,000, the milk growth factors being modified by transient acidification.

Alternatively or in addition, the milk product extract may be modified to enhance activity by the addition of one or more growth factors including but not limited to IGF-I, IGF-II, TGFβ, EGF, transforming growth factor α (TGFα), platelet-derived growth factor (PDGF), fibroblast growth factor (FGF) and keratinocyte growth factor (KGF).

The present invention may be applied in relation to any type of chemotherapy or radiation treatment that causes damage to the lining of the alimentary tract. Examples include, but are not limited to, alkylating agents such as mechlorethamine, melphalan and busulphan, antimetabolites including cytarabine, floxuridine, 5-fluorouracil, mercaptopurine, methotrexate and thioguanine, cytotoxic drugs such as bleomycin, actinomycin-D, daunorubicin, etoposide, mitomycin, vinblastine and vincristine, and other drugs such as hyroxyurea and procarbazine, as well as tissue-specific or total body irradiation. Any combination of these drugs and radiation regimens may be applicable to the present invention.

The milk product extract may be administered by any suitable route, including the oral, enteral or systemic route. Preferably, the milk product extract is administered directly into the alimentary canal by oral delivery or other means of direct enteral administration, in order to maximise the effective dose reaching the affected tissue.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; as a mouthwash or as an oil-in-water liquid emulsion or a water-in-oil liquid emulsion. The active ingredient may also be presented as a bolus, electuary or paste.

Compositions suitable for parenteral administration include aqueous and non-aqueous sterile injection solutions which may contain anti-oxidants, buffers, bacteriostats and solutes; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the compositions of this invention may include other agents conventional in the art having regard to the type of composition in question, for example, those suitable for oral administration may include such further agents as sweeteners, thickeners and flavouring agents.

The milk product extract may be administered at any appropriate time including prior to, during or after chemotherapy or radiation.

The milk product extract may be useful in combination with known chemotherapeutic agents. If formulated as a fixed dose, such combination products employ the milk product extract in an appropriate dosage range and the other pharmaceutically active agent within its approved dosage range. Compositions of the invention may be used sequentially with known chemotherapeutic agents when a combination formulation is inappropriate.

When the milk product extract is administered to a human subject the daily dosage can be determined by the attending physician with the dosage generally varying according to the age, weight, and response of the individual patient, as well as the severity of the patient's symptoms. In general a suitable dose of the compound of the invention will be in the range of 10 mg to 10 g per kilogram body weight of the recipient per day, preferably in the range of 100 mg to 1 g per kilogram body weight per day. However, the dose will also depend on the formulation and purity of the milk product extract used. The abovementioned doses are calculated on GFE or GFE-2 and could be modified accordingly by a person skilled in the art if a product of different activity or purity was used.

The present invention will now be more fully described with respect to the following examples. It should be understood, however, that the description following is illustrative only, and should not be taken in any way as a restriction of the generality of the invention described above.

IN THE FIGURES

FIG. 1. Oral administration of a milk product extract (GFE-2) for 5 days to methotrexate-injected rats reduces (a) the loss of mucosal crypt area in the jejunum and ileum, and (b) loss of mucosal villus length in the jejunum and ileum.

FIG. 3. Oral administration of a milk product extract (GFE-2) for up to 12 days to methotrexate injected rats reduces (a) the incidence of rats showing bacterial translocation, and (b) the number of bacterial colonies per gram of intestinal lymph node.

INTRODUCTION TO EXAMPLES

Surprisingly, a milk product extract from cheese whey, equivalent to GFE-2 in Australian Patent 645589 has been found by the applicants to reduce the severity of intestinal mucositis caused by injection of rats with the chemotherapy agent, methotrexate.

This same milk product extract has been found by the applicants to reduce the severity of oral mucositis in the hamster cheek pouch caused by injection in the hamsters with the chemotherapy agent, 5-fluorouracil.

In accordance with the above, treatment of chemotherapy or radiotherapy patients with GFE-2 would at least partially alleviate the symptoms of gut mucositis including mucosal damage, functional impairment, and susceptibility to infection, as well as at least partially alleviating the symptoms of oral and oesophagael mucositis, thereby facilitating recovery and potentially increasing tolerance to higher doses of chemotherapy drug or radiation.

EXAMPLE 1

Oral administration of a milk product extract from bovine cheese whey (GFE-2) partially prevents loss of small intestinal crypts and villi in rats with methotrexate-induced small bowel mucositis In this Example, rats were injected with high doses of the chemotherapy agent, methotrexate, as an experimental model of gut mucositis. In rats, methotrexate damages the small bowel, but not the oral or colonic mucosa (Vanderhoof J A, Park J H Y, Mohammadpour H, Blackwood D 1990 Effects of dietary lipids on recovery from mucosal injury. Gastroenterology. 98:1226–1231.) Oral administration to methotrexate-injected rats of a milk product extract purified from bovine cheese whey (GFE-2 as described in Australian Patent 645,589) provided evidence that the milk product extract can ameliorate chemotherapy damage to the small bowel.

Male Sprague Dawley rats, weighing on average 140 g and maintained in metabolism cages were fed a high-carbohydrate diet. Control rats received no milk product extract, whereas experimental rats were treated for 5 days with a milk product extract purified from bovine cheese whey. The whey-derived milk product extract (Whey Growth Factor Extract) was prepared as described for GFE-2 in Australian Patent 645,589. GFE-2 treated rats were fed a modified diet containing 31.2 g GFE-2/kg diet in place of the equivalent amount of casein. In addition, the GFE-2 fed rats were given GFE-2 by stomach gavage on days 3, 4 and 5 of the experimental period so that the total dose of GFE-2 per day averaged 514 mg/day GFE-2. Control rats were fed the unmodified diet and gavaged by an identical protocol on days 3, 4 and 5 with an equivalent amount of bovine serum albumin to ensure an isonitrogenous diet.

One group of control rats and the GFE-2 treated rats (8 rats per group) were injected subcutaneously with 2.5 mg/kg methotrexate at the start of days 1, 2 and 3 according to the protocol described by Vanderhoof et al (1990), the entire disclosure of which is incorporated herein by reference. An additional control group ('pair-fed') received sham methotrexate injections, and was pair-fed to the methotrexate-injected control group.

Rats were maintained in the metabolism cages for 5 days, at which time they were killed for collection of the gastrointestinal tract. Tissue samples were collected from the proximal small bowel (duodenum and jejunum) as well as the distal small bowel (ileum). Tissue samples were fixed in methacarn, embedded in paraffin, sectioned and stained with haematoxylin-eosin for histological analysis using methods described in Read et al (1992), the entire disclosure of which is incorporated herein by reference (Read L C, Tomas F M, Howarth G S, Martin A A, Edson K J, Gillespie C M, Owens P C, Ballard F J 1992 Insulin-like growth factor-I and its N-terminal modified analogues induce marked gut growth in dexamethasone-treated rats. J Endocrinol. 133:421–431).

Figure 1A:
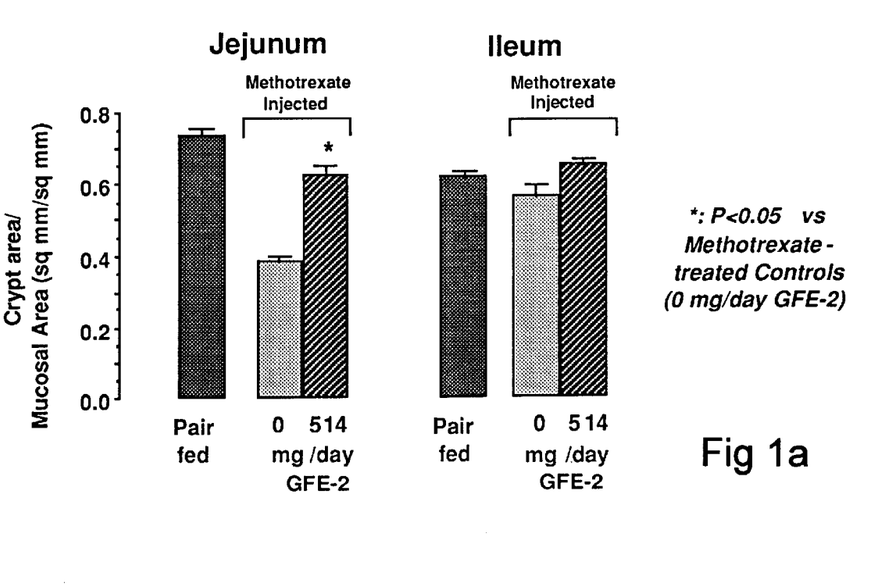

Compared with the pair-fed controls, the methotrexate-injected control group showed loss of mucosal crypts in the jejunum, and to a lesser extent in the ileum. This is illustrated in FIG. 1(a) as the area of intact crypts per unit area of total mucosa, and demonstrates that methotrexate causes loss of mucosal crypts (which contain the dividing cells of the epithelium) characteristic of chemotherapy damage. Also characteristic of chemotherapy damage in the small bowel, methotrexate injection caused stunting and loss of intestinal villi, being the functional compartment of the small bowel mucosa. This is illustrated in FIG. 1(b) by a reduction in the surface length of the finger-like villi per unit length of intestinal circumference in methotrexate-treated controls compared with the pair-fed group receiving no methotrexate.

Figure 1B:
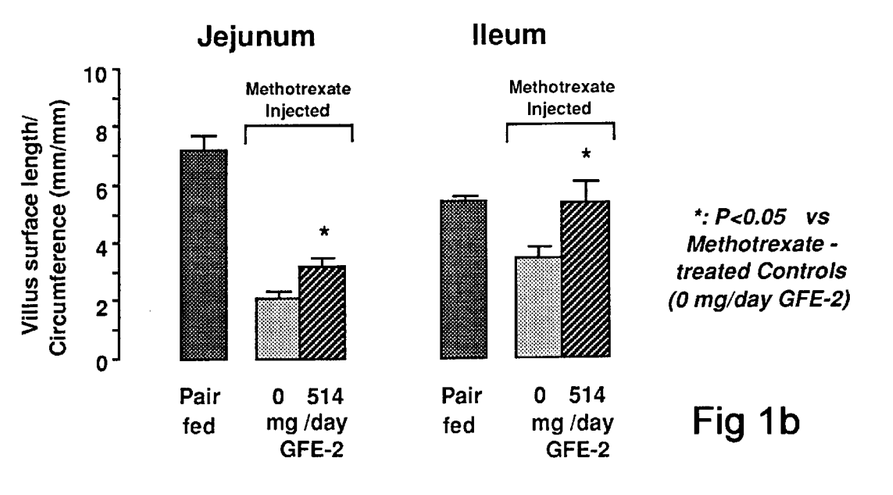

Oral administration of GFE-2 for 5 days starting at the time of the first methotrexate injection partially prevented the loss of mucosal crypts and villi in both regions of the small bowel (FIG. 1). The effects of GFE-2 were statistically significant (P<0.05 by ANOVA) in the jejunum, where methotrexate-induced damage was more severe, and in the ileum for villus surface length. The example demonstrates that oral administration of GFE-2 is able to partially prevent or accelerate repair of chemotherapy damage in the small bowel.

EXAMPLE 2

Sucrase activity in the mucosa of rats from Example 1

From the same experiment as described in Example 1, 4 cm lengths of small bowel were frozen for measurement of the activity of mucosal sucrase, an enzyme located on the surface of epithelial cells of the villus. Because sucrase is essential for digestion of dietary sucrose, the sucrase activity per unit length of intestine provides a measure of the functional capacity of the small bowel (Read et al, 1992).

Figure 2:
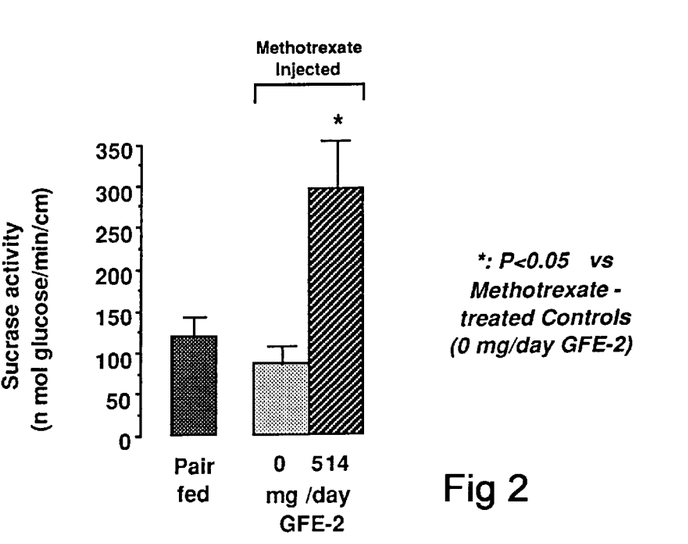
FIG. 2. Oral administration of a milk product extract (GFE-2) for 5 days to methotrexate-injected rats increases the sucrase activity of the mucosa in the ileum.

Five days' oral administration of GFE-2 to methotrexate-injected rats significantly improved ($P<0.05$) the sucrase activity per unit length of ileum compared with the methotrexate-injected control group, or the pair-fed control group (FIG. 2).

This example demonstrates that GFE-2 improves the functional capacity of the chemotherapy-damaged small bowel.

EXAMPLE 3

Oral administration of GFE-2 to rats for 5 to 12 days reduces bacterial translocation across the gut.

The ability of the gut epithelium to provide a barrier against bacterial invasion provides another measure of gut function that is compromised by gut mucositis.

In Example 3, 140 g male Sprague Dawley rats were injected with methotrexate for three consecutive days as described in Example 1. Methotrexate-injected rats were administered oral GFE-2 by an identical protocol to that described in Example 1. One group of rats was killed on day 5 after the start of methotrexate injections (as in Example 1), while in other groups, GFE-2 treatment was continued for a total of 8 or 12 days (8 rats per group). Control methotrexate-treated rats and pair-fed control rats identical to those in Example 1 were killed on days 5, 8 and 12 (8 rats per group).

Rats were maintained in metabolism cages as in Example 1 until exsanguination on day 5, 8 or 12. The abdominal skin was soaked in 70% ethanol before the intestine was removed under aseptic conditions. All visible mesenteric lymph nodes were placed into a sterile pre-weighed container. Samples were then weighed and brain heart infusion solution was added to a final concentration of 100 mg/ml. Tissues were homogenised in this solution with sterile glass-reinforced grinders. For measurement of translocation of gram negative bacteria into mesenteric lymph nodes, 40 or 60 mg of each tissue homogenate was placed onto MacConkey agar II or blood agar plates and incubated aerobically at 35° C. for 48 hours. Enteric gram negative bacterial colonies were identified using API 20E strips, then counted. The incidence (proportion of animals exhibiting detectable bacterial translocation) and mean number of bacterial colonies per gram of tissue were calculated for each treatment group.

Figure 3A:
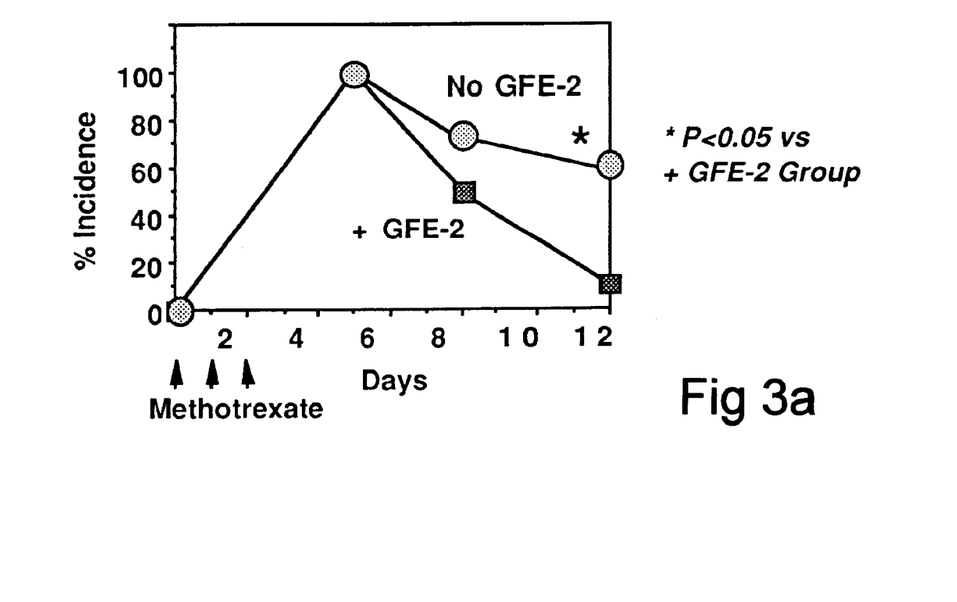
Figure 3B:
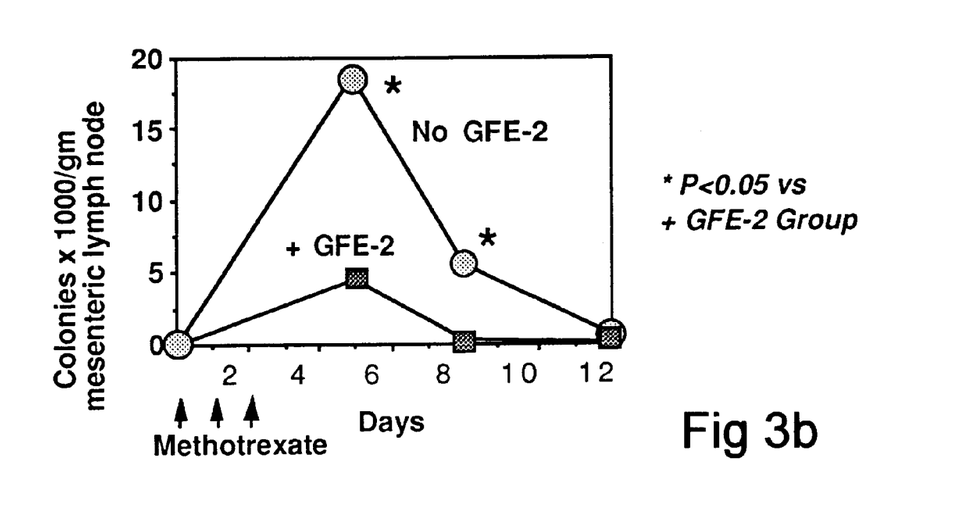

Pair-fed control animals receiving no methotrexate showed no incidence of bacterial translocation across the gut. Methotrexate injection impaired the intestinal barrier so that all rats in the methotrexate-injected control group (FIG. 3: 'No GFE-2') had positive bacterial cultures from mesenteric lymph nodes on day 5. The incidence in this group diminished over the next 7 days, but remained at 60% of rats on day 12 (FIG. 3a). The number of colonies per gram of mesenteric lymph node was maximal on day 5, and then diminished thereafter in parallel with the incidence (FIG. 3b).

Oral administration of GFE-2 resulted in a lower incidence of translocation on days 8 and 12, with the difference between GFE-2 treated and control methotrexate-injected rats reaching statistical significance by $\chi^2$ test ($P<0.05$) on day 12. The number of colonies per gram of mesenteric lymph node was also significantly lower in the GFE-2 treated group on both day 5 and 8.

The example demonstrates that oral administration of the milk product extract partially prevents chemotherapy-induced loss of barrier function in the gut. This could be expected to decrease the incidence of infection and sepsis following chemotherapy.

EXAMPLE 4

Milk product extracts protect intestinal cells in culture against damage by the chemotherapy agent, methotrexate.

The milk product extracts evaluated in this Example were GFE-2 prepared as described in Australian Patent 645,589, transiently acidified GFE-2 prepared as in Example 2 of International Patent Application PCT/AU95/00237 and the permeate fraction obtained by controlled pore ultrafiltration under acid conditions of GFE-2 as described in Example 5 of International Patent Application PCT/AU95/00237.

Intestinal epithelian cells (IEC-6) were plated on to plastic 96-well plates at a density of $2.5\times10^4$ cells/ml in Dulbecco-Modified Eagle's Minimal Essential Medium (DMEM) containing 10% fetal bovine serum. The plates were incubated in a humidified atmosphere at 37° C. in the presence of 5% $CO_2$ for 1 day after which the medium was replaced and the incubation continued for a second day.

On the third day the medium in each well was replaced by 100 $\mu l$ of a methotrexate solution ($10^{-6}$M in DMEM plus 10% fetal bovine serum) plus 100 $\mu l$ of a milk product extract solution containing either GFE-2, transiently acidified GFE-2 or permeate GFE-2 at various dilutions in DMEM plus 10% fetal bovine serum.

The cells were left in contact with these solutions for one day. The wells were then washed twice with DMEM and incubated for a further day in DMEM containing 10% fetal bovine serum.

Figure 4:
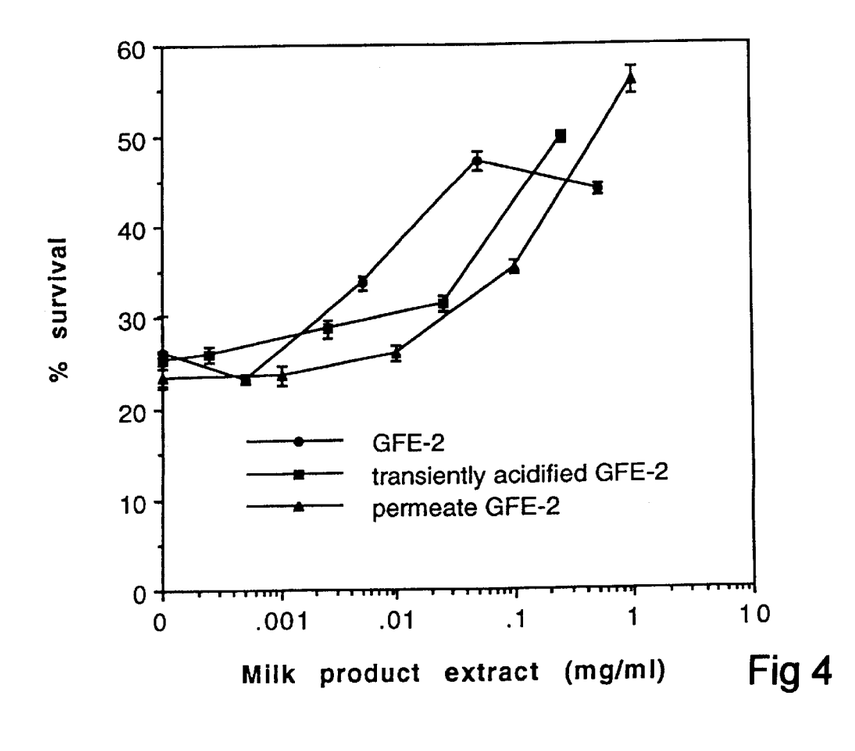
FIG. 4. Administration of milk product extracts (GFE-2, transiently acidified GFE-2 and permeate GFE-2) concurrently with methotrexate to cultured intestinal cells (IEC-6) in culture for 24 hours enhances the survival of the cells in a dose dependent manner.

After incubation of the cells in this fresh medium for one day the cells were washed, fixed and the cell numbers quantified using an automated methylene blue method (M H Oliver et al., J. Cell Sci. 92, 513, 1989, the entire disclosure of which is incorporated herein by reference). Growth is expressed as the percentage survival of cells relative to cells not exposed to methotrexate. The results are illustrated in FIG. 4.

The experiment demonstrates dose-dependent increases in survival of the intestinal cells with all three examples of milk product extract.

EXAMPLE 5

Continuous topical application of GFE-2 to the hamster cheek pouch reduces the severity of 5-fluorouracil (5-FU)-induced chemotherapy-induced mucositis This experiment investigated the effects of GFE-2 administered topically on chemotherapy-induced oral mucositis in male Golden Syrian hamsters. The trial included continuous treatment of GFE-2 to the cheek pouch of 10 hamsters treated with 5-fluorouracil.

Hamsters were divided into two groups of five animals. The initial mean body weight of each group was similar. All hamsters were given intraperitoneal injections of 90 mg/kg of 5-FU on day 1, and 60 mg/kg on day 3. The cheek pouch was scratched on days 1, 2 and 3 with six strokes of a wire brush in one direction and six strokes in the other perpendicular direction to achieve a uniform wound.

Groups were treated with either a commercial mouthwash as vehicle, or 0.3 ml of GFE-2 at 40 mg/ml protein concentration. The cheek pouch liquid treatments were applied daily for one minute, during which time the hamsters were anaesthetised using isoflurane anaesthesia.

The cheek pouch was assessed on days 5, 7, 8, 11, 13 and 15. Monitoring was based on a visual assessment of the cheek pouch (graded on a 1–10 scale) taking into account the overall severity of the lesion, degree of bruising, swelling and scarring. Body weight was recorded as a percentage of the day 0 value.

Figure 5:
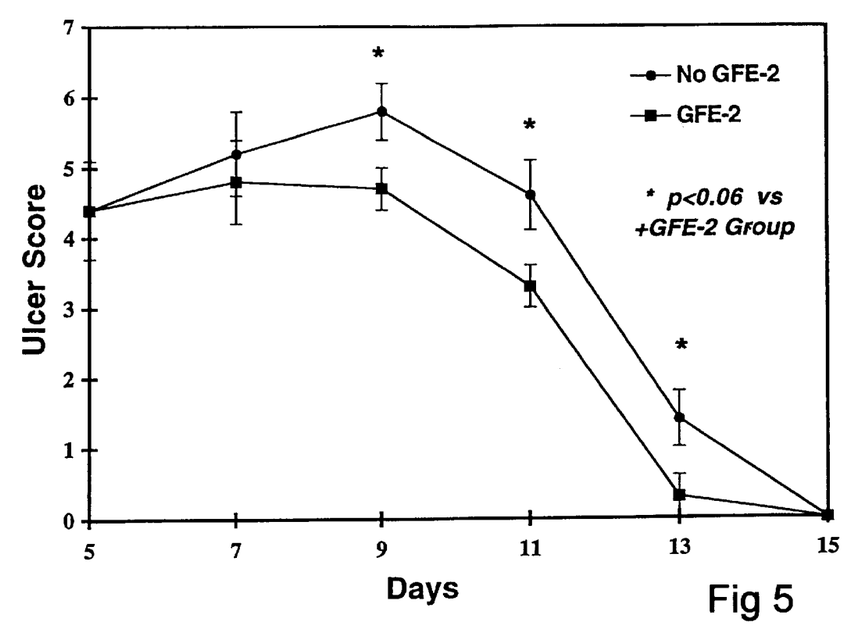
FIG. 5. Daily treatment of the cheek pouch in hamsters with a milk product extract (GFE-2) reduces the severity of oral mucositis ulcers caused by 5-fluorouracil.
Figure 6:
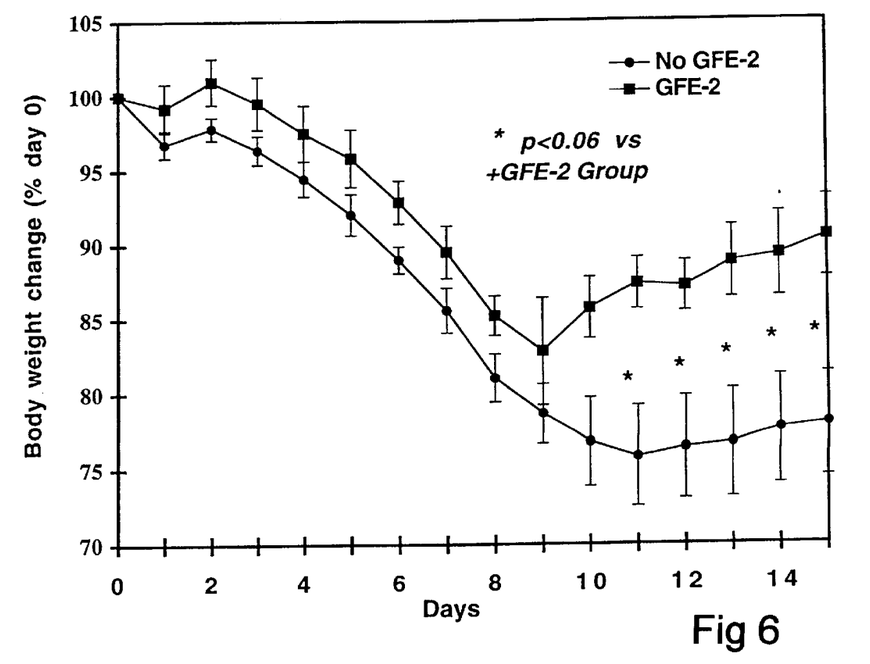
FIG. 6. Daily treatment of the cheek pouch in hamsters with a milk product extract (GFE-2) reduces the body weight loss induced by 5-fluorouracil.

Animals given a topical treatment of GFE-2 showed reduced mucositis compared to the vehicle treated group, measured as overall visual score (FIG. 5), total ulcer area and body weight loss (FIG. 6). Each of these effects was statistically significant by paired t-test favouring GFE-2 treatment.

This example suggested that topical administration of GFE-2 may reduce the severity of oral mucositis and related symptoms such as body weight loss.

Finally, it is to be understood that various other modifications and/or alterations may be made without departing from the spirit of the present invention as outlined herein.

What is claimed is:

1. A method for ameliorating damage to the lining of the alimentary tract of a patient who will be administered a chemotherapeutic agent, said method comprising administering to the patient an effective amount of an extract of a human or animal milk product, said extract comprising a plurality of cell growth stimulating factors having basic to approximately neutral isoelectric points, said extract being enriched in said factors as compared to the milk product naturally, said administering occurring prior to or concurrent with the administration of the chemotherapeutic agent.

2. A method according to claim 1 wherein the milk product extract is a cheese whey extract, a colostral whey extract, a skim milk extract or an acid casein whey extract.

3. A method according to claim 2 wherein the milk product extract is prepared by subjecting a milk product to cation exchange chromatography.

4. A method according to claim 3 wherein the milk product extract is a milk product extract composition including the plurality of cell growth stimulating factors having basic to about neutral isoelectric points, wherein the mixture of cell growth factors is obtained from a milk product of an ungulate mammal, and wherein the milk product is subjected to a cation exchange matrix under conditions whereby casein, α lactalbumin, and β lactoglobulin present in the milk product are not adsorbed to the matrix, after which the adsorbed growth factor mixture is eluted with a substantially aqueous salt solution and then optionally concentrated.

5. A method according to claim 2 wherein the milk product extract includes lactoperoxidase and/or lactoferrin.

6. A method according to claim 2 wherein the milk product extract is GFE or GFE-2.

7. A method according to claim 1 wherein the milk product extract is modified by transient acidification to enhance activity.

8. A method according to claim 1 wherein the milk product extract is modified to enhance activity by the addition of one or more growth factors comprising IGF-I, IGF-II, TGFβ, EGF, transforming growth factor α (TGFα), platelet-derived growth factor (PDGF), fibroblast growth factor (FGF) or keratinocyte growth factor (KGF).

9. A method according to claim 1 wherein the damage includes damage to the lining of the mouth and/or oesophagus.

10. A method according to claim 9 wherein the damage includes mucositis.

11. A method according to claim 1 wherein the damage includes at least partial loss of mucosal crypt area and/or mucosal villus length.

12. A method according to claim 1 wherein the damage includes an increase in bacterial translocation across the alimentary tract.

13. A method according to claim 1 further comprising the step of administering the chemotherapeutic agent to the patient after or concurrent with administration of the milk product extract.

14. A method according to claim 13, wherein the chemotherapeutic agent is administered to the patient within two days after administering the milk product extract.

15. A method according to claim 1, wherein the milk product extract is administered to the patient as a topical administration.

16. A method according to claim 15, wherein the topical administration comprises applying the milk product extract to a lining of the mouth of the patient.

17. A method according to claim 1, wherein the milk product extract is administered to the patient orally, either alone or in a composition that consists essentially of the milk product extract and a pharmaceutically or veterinarily acceptable diluent, carrier or excipient.

18. A method according to claim 1, wherein the milk product extract is topically administered to the mouth of the patient in a composition that consists essentially of the milk product extract and a liquid that is selected and is present in the composition in an amount sufficient to render the composition suitable as a mouthwash.

19. A method according to claim 1, wherein the milk product extract is administered to the patient in a composition that consists essentially of the milk product extract and the chemotherapeutic agent.

20. A method according to claim 13 wherein the chemotherapeutic agent comprises mechlorethamine, melphalan, busulphan, cytarabine, floxuridine, 5-fluorouracil, mercaptopurine, methotrexate, thioguanine, bleomycin, actinomycin-D, daunorubicin, etoposide, mitomycin, vinblastine, vincristine, hyroxyurea or procarbazine or mixtures thereof.

* * * * *